United States Patent [19]

Lugojan

[11] Patent Number: 5,543,023
[45] Date of Patent: Aug. 6, 1996

[54] GEL ELECTROPHORESIS CASSETTE

[75] Inventor: Petru P. Lugojan, Akron, Ohio

[73] Assignee: Biotech Holdings, Inc., Hudson, Ohio

[21] Appl. No.: 539,235

[22] Filed: Oct. 4, 1995

[51] Int. Cl.$^6$ .......................... G01N 27/26; G01N 27/447
[52] U.S. Cl. ........................................... 204/618; 204/619
[58] Field of Search ...................... 204/616, 618, 204/619, 620, 470, 466, 467

[56] References Cited

U.S. PATENT DOCUMENTS

| | | | |
|---|---|---|---|
| 3,450,624 | 6/1969 | Natelson | 204/621 |
| 3,479,265 | 11/1969 | Eleitch | 204/620 |
| 3,879,280 | 4/1975 | Peterson et al. | 204/299 R |
| 4,035,377 | 7/1977 | Detroy | 204/299 R |
| 4,130,471 | 12/1978 | Grunbaum | 204/299 R X |
| 4,294,684 | 10/1981 | Serwer | 204/620 X |
| 4,417,967 | 11/1983 | Ledley | 204/182.8 |
| 4,909,918 | 3/1990 | Bambeck et al. | 204/619 |
| 4,909,977 | 3/1990 | Hurd et al. | 204/620 X |
| 5,073,246 | 12/1991 | Chu et al. | 204/619 |
| 5,164,065 | 11/1992 | Bettencourt et al. | 204/619 |
| 5,232,573 | 8/1993 | Rosenvold | 20/620 |
| 5,275,710 | 1/1994 | Gombocz et al. | 204/461 |
| 5,281,322 | 1/1994 | Antoinette et al. | 204/299 R |
| 5,284,565 | 2/1994 | Chu et al. | 204/619 |
| 5,288,465 | 2/1994 | Margolis | 204/299 R X |
| 5,304,292 | 4/1994 | Jacobs et al. | 204/299 R |
| 5,324,412 | 6/1994 | Kolner | 204/619 |
| 5,407,522 | 4/1995 | Insalaco et al. | 156/465 |

*Primary Examiner*—John Niebling
*Assistant Examiner*—John S. Starsiak, Jr.
*Attorney, Agent, or Firm*—Pearne, Gordon, McCoy & Granger

[57] ABSTRACT

A gel electrophoresis cassette for conducting gel electrophoresis separations. The cassette has a first plate, a second plate spaced apart from the first plate by spacer members, and an electrophoresis gel layer between the plates. The second plate is plastic and has lane dividers molded integrally therewith. The lane dividers are in releasable sealing engagement with the first plate, the releasable sealing engagement being provided by a means selected from the group consisting of (1) a film carrier coated on each side with a pressure sensitive adhesive and (2) ultrasonic welding. A niche is provided in one of the spacer members, the niche being effectively sized and positioned to receive the tip of an instrument such as a screwdriver effective to pry apart the plates after the gel is run so the gel layer can be removed for analysis.

10 Claims, 1 Drawing Sheet

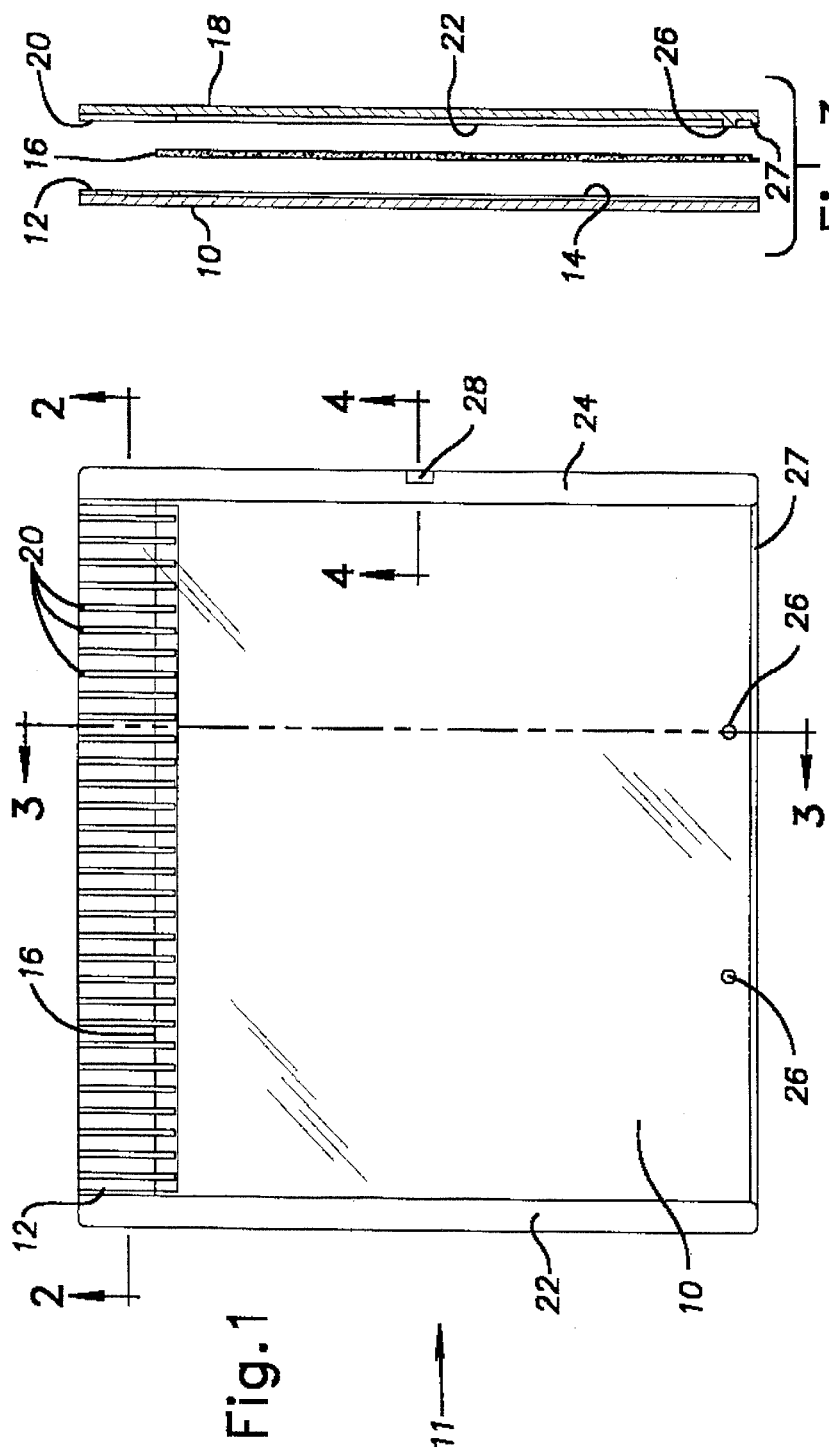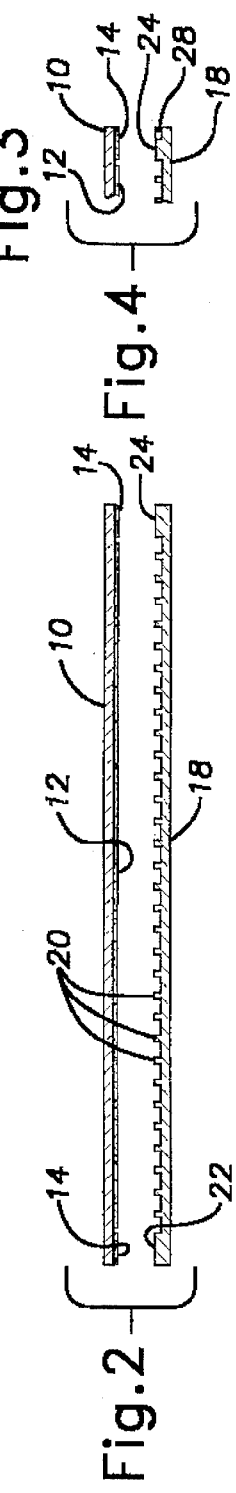

5,543,023

GEL ELECTROPHORESIS CASSETTE

BACKGROUND OF THE INVENTION

This invention relates to a gel electrophoresis cassette useful for conducting gel electrophoresis separations.

DESCRIPTION OF RELATED ART

In the process of electrophoresis a complex mixture of macromolecules is resolved or separated on the basis of charge and/or size under the influence of an electric field and is a primary tool in biochemistry, used to separate complex mixtures of molecules such as proteins or nucleic acids into their individual components. Electrophoretic analysis is based upon the fact that each molecule is characterized by a particular electrophoretic mobility under a given set of conditions. Macromolecules will migrate within a voltage gradient according to their net charge and will reach equilibrium at their isoelectric point at which their net mobility will be zero.

It is common practice to use a cassette for conducting gel electrophoresis, the cassette comprising two flat plates, usually transparent glass or plastic, separated by separators or spacers or other spacer means. In order to provide a buffered gel between the plates, a suitable separation gel medium or electrophoresis gel such as agarose or a polyacrylamide is provided, in liquid form, into the space or void volume between the plates and allowed to polymerize therein. In order to provide accurate sample resolution, it is necessary that the electrophoresis gel composition be uniform and that the gel thickness be uniform. These conditions are necessary in order to avoid factors which effect molecular electrophoretic mobility other than the characteristics of the molecules being separated. In use, the cassette with gel is positioned between two buffer solutions after the sample or samples have been placed on the gel at one end of the cassette. A voltage is applied between the buffers which causes the samples to migrate within the gel. Upon completion of sample separation, the gel is typically separated from the plates for analysis.

The art of gel electrophoresis is generally well-known and the contents of U.S. Pat. Nos. 5,281,322; 5,164,065; 5,232,573; 5,324,412; 5,304,292; 5,284,565; 5,073,246; and 4,909,918 are incorporated herein by reference.

In the prior art, sample wells are formed at a top end of the cassette by means of a removable piece or "comb" having fingers having the desired shape of the wells. The comb is positioned so that the fingers extend into the gel while it is polymerizing. After the gel is set, the fingers are removed from the gel to leave wells wherein samples can be positioned. The use of the comb is disadvantageous because an additional manipulative step is required and the set gel may be ripped when the fingers are removed.

Alternatively, as disclosed in U.S. Pat. No. 4,909,918, a ridged piece of plastic may be partially inserted into the gel and left to remain there to define sample wells. However, in this approach samples may leak into adjacent wells. Other prior art patents disclose the use of lane dividers between the plates to define sample wells. However, these references do not teach effective, convenient and useful means to seal the lane dividers to the adjacent plates to prevent leakage from one well to adjacent wells.

There is a need for a cassette which does not require the use of a removable comb to form the wells, and which more effectively and conveniently prevents samples from leaking into adjacent wells.

SUMMARY OF THE INVENTION

A cassette for conducting gel electrophoresis is provided, comprising a first plate, a second plate, and an electrophoresis gel layer between the two plates. The second plate is plastic and is spaced apart from the first plate by spacer means. The second plate has lane dividers molded integrally therewith, the lane dividers being biased against the first plate and in releasable sealing engagement therewith. The releasable sealing engagement is provided by a means selected from the group consisting of (1) a film carrier coated on each side with a pressure sensitive adhesive and (2) ultrasonic welding. The lane dividers extend at least partially into the gel layer. The gel layer, lane dividers, and first and second plates define wells suitable for receiving samples for gel electrophoresis separation.

BRIEF DESCRIPTION OF THE DRAWINGS

FIG. 1 is a front elevational view of the cassette of the present invention.

FIG. 2 is a sectional view, in exploded form, taken along line 2—2 of FIG. 1.

FIG. 3 is a sectional view, in exploded form, taken along line 3—3 of FIG. 1.

FIG. 4 is a sectional view, in exploded form, taken along line 4—4 of FIG. 1.

DETAILED DESCRIPTION OF THE PREFERRED EMBODIMENTS OF THE INVENTION

Referring to FIGS. 1–3, a gel electrophoresis cassette 11 is shown, which is preferably used for vertical gel electrophoresis. The cassette 11 comprises a first plate 10 and a second plate 18. As shown in FIG. 1, the cassette has a first side or side portion on the left (where item 22 is denoted), and a second side or side portion on the right (where item 24 is denoted). In FIG. 3, the lines extending from numerals 10 and 18 contact the outside surfaces of plates 10 and 18, respectively. The inner surfaces of plates 10 and 18 face the gel layer 16. Plate 10 is rigid, preferably flat, and preferably glass or transparent plastic. Plate 18 is rigid, preferably flat except for the features noted, and preferably transparent plastic. The plastic for the plates is preferably polystyrene. Plates 10 and 18 are each one-piece structures. Preferably molded integrally with plate 18 are lane dividers 20, first spacer member 22, second spacer member 24, spacer posts 26 and holding ridge 27. The spacer members 22 and 24 extend along the sides and run the length of the plate and, as spacer means, hold the plates in spaced apart relationship when the cassette is assembled. Spacer posts 26 also function to maintain the plates in spaced apart relationship. As shown in FIG. 1, lane dividers 20 extend down from the top of plate 18, preferably at least about ⅛ of the length of the plate. As shown in FIG. 2, each lane divider 20 is preferably about 1 mm wide and is non-electrically-conductive plastic and extends upwards or away from the plate, preferably the same distance as the spacer members and the spacer posts, this distance, but for the tape sealing means, defining the thickness of the gel layer and generally being about 0.5–1.5 mm, frequently about 1 mm. The lane dividers are evenly spaced apart so each well will be the same size and there is no electrically-conductive gel between adjacent lane dividers. The holding ridge 27 extends along substantially the entire bottom edge of plate 18, as shown in FIGS. 1 and 3, and extends upwards or away from plate 18 a portion, preferably half, of the distance or gap between the two plates when assembled (this distance or gap being filled by the gel layer), leaving a gap so that the gel layer 16 may communicate with the buffer solution as known in the art. As shown in FIG. 3, post 26 extends across the entire gap or gel layer to contact plate 10; ridge 27 extends only part-way, leaving the above-mentioned gap for communication. The purpose of ridge 27 is to assist in preventing the gel layer 16 from sliding out of the cassette when mounted vertically.

When the cassette is assembled, the sides of the cassette are preferably releasably sealed with strips of double-sided adhesive tape 14, which correspond with the spacer members 22 and 24 and seal the plate 10 to the spacer members, the spacer members thus being in releasable sealing engagement with the plate 10. The strips 14 can be first applied to either the plate 10 or the spacer members before final assembly of the cassette, and eliminate the need to seal the cassette by adhesive tape along the outside of the cassette. Preferably the cassette is free from the presence of sealing tape at the sides of the cassette extending from the outside surface of the first plate to the outside surface of the second plate around each side of the cassette. The strips 14 are preferably a thin polyester film carrier coated on each side with a high performance, acrylic-based, pressure sensitive adhesive, such as Product IB-2100 from Mactac, 4560 Darrow Rd., Stow, Ohio 44224, which product has 4 lbs/in$^2$ quick tack stainless steel, 5 lbs/in. peel adhesion stainless steel 30 min., shear of 300+ hours to fail—stainless steel 2 psi at 72° F., 10 lbs/in. tensile strength MD and CD, 100% elongation MD and 90% elongation CD, and 0.132 mm thickness—carrier plus adhesive.

An important feature of the invention is to prevent leakage between adjacent wells defined by the lane dividers 20. This can be accomplished by applying a strip of double-sided adhesive tape 12 to the top of plate 10 so that the full length of each lane divider 20 will be releasably sealed by the tape. When the two plates are assembled together, the lane dividers 20 are biased against the first plate and are pressed into the strip 12 to seal against leakage, yet after the sample is run, the two plates may be pried apart with the lane dividers releasing from the adhesive strip (so the gel may be removed), the lane dividers thus being in releasable sealing engagement with the first plate 10. The lane dividers are not cracked, broken or rendered nonreusable by this releasing procedure, which is nondestructive. The strip 12 is preferably a thin 0.5 mil polyester film carrier coated on each side with a heavy coating of an aggressive, high performance, acrylic-based pressure sensitive adhesive, such as Product IB-2100 from Mactac, described above. Strips 14 and 12 are preferably transparent.

Alternatively, and more preferably, the lane dividers are releasably sealed to the first plate by ultrasonic welding. Ultrasonic welding is a well-known joining technique in which ultrasonic vibratory energy is transmitted to melt a thermoplastic material and bond it to a substrate. See, for example, Kirk-Othmer, *Concise Encyclopedia of Chemical Technology*, John Wiley & Sons, Inc., New York, 1985, page 1204. Typical ultrasonic welding equipment is available from Branson Ultrasonics Corporation, Danbury, Conn. 06813. In this case the ultrasonic welding joint is made in a sealing manner so that the sample cannot leak out, but also weak enough so that the sealing engagement is releasable, that is, the two plates may be pried apart after the sample is run, breaking the ultrasonic weld seal joint, so that the gel may be removed. The sides of the cassette may also optionally be releasably sealed by ultrasonic welding. If both plates are plastic, ultrasonic welding is preferred over double-sided adhesive tape.

Referring to FIGS. 1 and 4, there is shown a niche 28 provided in plate 18. The niche extends partway into the spacer member 24 and is sized and positioned to receive the tip of a screwdriver or similar-tipped instrument to pry apart the two plates after the gel is run. Without the niche it is hard to pry apart or separate the two plates to remove the gel for analysis. By use of the means described above, the two plates are removably or releasably secured together.

As is known in the art, an electrophoresis gel, such as a polyacrylamide gel, is provided between the plates as electrophoresis gel layer 16. The gel is provided so that it covers at least a minor lower portion of the lane dividers and sets without use of a comb. As shown in FIGS. 1 and 3, a minor portion, such as ½, of each lane divider 20 extends into the gel layer 16 to prevent leakage between wells. As is known in the art, the gel layer generally consists of a running gel and optionally a stacking gel. The gel layer may be of the non-denaturing type (no detergent in the gel) or the denaturing type (with detergent, such as SDS, in the gel). The denaturing, type gel is particularly active in attacking the prior art adhesives (such as adhesive tape or sealing tape on the exterior of the cassette) at the sides of the cassette. The adhesive tape strips 14 of the present invention are especially resistant to denaturing type gel attack and are effective to keep the cassette from leaking when stored flat at 4° C. for three months without the presence of sealing tape at the sides of the cassette extending from the outside of one plate to the outside of the other plate around each side portion.

If both plates 10 and 18 are plastic, one or both of their inner surfaces (the inner surface contacts the gel layer) must be surface treated as is known in the art so that the gel layer will not slide out, or alternatively a film, referred to in the specification and claims as a surface active film, such as GelBond PAG film from FMC BioProducts, Rockland, Me. 04841 may be applied to or attached to an inner plastic surface as is known in the art, so that the gel layer will adhere to the film and not slide out.

If plate 10 is glass and plate 18 is plastic, the glass plate, the inner surface (the surface contacting the gel layer) of which is untreated, provides enough adhesion to the gel that the inner surface of the plastic plate need not be surface treated. This is an advantage of the present invention when plate 10 is glass and plate 18 is plastic.

In operation, samples are placed in the wells defined by the lane dividers and the gel electrophoresis separation is performed. Then the plates are pried apart and the gel is removed for analysis.

Although the preferred embodiments of the invention have been shown and described, it should be understood that various modifications and rearrangements of the parts may be resorted to without departing from the scope of the invention as disclosed and claimed herein.

What is claimed is:

1. A cassette for conducting gel electrophoresis comprising a first plate, a second plate, and an electrophoresis gel layer between said first plate and said second plate, said second plate being plastic and being spaced apart from said first plate by spacer means, said second plate having lane dividers molded integrally therewith, said lane dividers being biased against said first plate and in releasable sealing engagement therewith, said releasable sealing engagement being provided by a means selected from the group consisting of (1) a film carrier coated on each side with a pressure sensitive adhesive and (2) ultrasonic welding, said lane dividers extending at least partially into said gel layer, said gel layer, lane dividers, and first and second plates defining wells suitable for receiving samples for gel electrophoresis separation.

2. A cassette according to claim 1, wherein said first plate is glass.

3. A cassette according to claim 1, said cassette having a first side portion and a second side portion, said spacer means comprising a first spacer member extending along said first side portion and a second spacer member extending along said second side portion, one of said spacer members having a niche effectively sized and positioned to receive the tip of an instrument effective to pry apart the first and second plates after the cassette is used for gel electrophoresis separation.

4. A cassette according to claim 1, said second plate having sides, said spacer means comprising first and second spacer members molded integrally with said second plate and extending along the sides thereof, at least one of said spacer members being in releasable sealing engagement with said first plate, said releasable sealing engagement being provided by a means selected from the group consisting of (1) a film carrier coated on each side with a pressure sensitive adhesive and (2) ultrasonic welding.

5. A cassette according to claim 4, said cassette having sides, said first and second plates having outside surfaces, said cassette being free from sealing tape at the sides of the cassette extending from the outside surface of the first plate to the outside surface of the second plate around each side of the cassette.

6. A cassette according to claim 5, said electrophoresis gel layer comprising denaturing type gel.

7. A cassette according to claim 1, wherein said first plate is plastic, further comprising a surface active film attached to an inner surface of one of said plates to assist in preventing said gel layer from sliding out of said cassette.

8. A cassette according to claim 3, said second plate having sides, said spacer means comprising first and second spacer members molded integrally with said second plate and extending along the sides thereof, at least one of said spacer members being in releasable sealing engagement with said first plate, said releasable sealing engagement being provided by a means selected from the group consisting of (1) a film carrier coated on each side with a pressure sensitive adhesive and (2) ultrasonic welding.

9. A cassette according to claim 8, said cassette having sides, said first and second plates having outside surfaces, said cassette being free from sealing tape at the sides of the cassette extending from the outside surface of the first plate to the outside surface of the second plate around each side of the cassette.

10. A cassette according to claim 1, said second plate having a bottom, said second plate having a ridge at its bottom effective to assist in preventing said gel layer from sliding out of said cassette.

* * * * *